(12) United States Patent
Lee et al.

(10) Patent No.: US 9,102,732 B2
(45) Date of Patent: Aug. 11, 2015

(54) ANTIBODIES AGAINST GLUCAGON RECEPTOR AND THEIR USE

(75) Inventors: Eunkyung Lee, Daejeon (KR); Seong-Kyung Seo, Daejeon (KR); Tae-Seong Kim, Daejeon (KR)

(73) Assignee: NEOPHARM CO., LTD. (KR)

( * ) Notice: Subject to any disclaimer, the term of this patent is extended or adjusted under 35 U.S.C. 154(b) by 369 days.

(21) Appl. No.: 13/394,463

(22) PCT Filed: Sep. 8, 2009

(86) PCT No.: PCT/KR2009/005084
§ 371 (c)(1),
(2), (4) Date: May 18, 2012

(87) PCT Pub. No.: WO2011/030935
PCT Pub. Date: Mar. 17, 2011

(65) Prior Publication Data
US 2013/0149315 A1      Jun. 13, 2013

(51) Int. Cl.
*A61K 39/395* (2006.01)
*C07K 16/28* (2006.01)
*A61K 39/00* (2006.01)

(52) U.S. Cl.
CPC ....... *C07K 16/2869* (2013.01); *A61K 2039/505* (2013.01); *C07K 2317/24* (2013.01); *C07K 2317/515* (2013.01); *C07K 2317/565* (2013.01); *C07K 2317/76* (2013.01)

(58) Field of Classification Search
None
See application file for complete search history.

(56) References Cited

U.S. PATENT DOCUMENTS

2009/0041784 A1* 2/2009 Yan et al. .................. 424/172.1
2011/0223160 A1* 9/2011 Yan et al. .................. 424/133.1

FOREIGN PATENT DOCUMENTS

WO     2008/036341     3/2008

OTHER PUBLICATIONS

Paul, W.E. Fundamental Immunology, Third Edition (textbook), "Fv Structure and Diversity in Three Dimensions" pp. 292-295; Raven Press, New York (1993).*
Rudikoff et al. Single amino acid substitution altering antigen-binding specificity Proc. Natl. Acad. Sci. USA, 79(6):1979-1983, (Mar. 1982).*
Casset et al. A peptide mimetic of an anti-CD4 monoclonal antibody by rational design. Biochem Biophys Res Comm. vol. 307:198-205 (2003).*
Bendig M. M. Humanization of rodent monoclonal antibodies by CDR grafting. Methods: A Companion to Methods in Enzymology, vol. 8:83-93 (1995).*
Portolano et al., Lack of Promiscuity in Autoantigen-Specific H and L Chain Combinations as Revealed by Human H and L Chain Roulette J. Immunol., vol. 150(3):880-887 (Feb 1993).*
International Search Report—PCT/KR2009/005084 dated Jun. 1, 2010.
Hai Yan, et al., "Fully Human Monoclonal Antibodies Antagonizing the Glucagon Receptor Improve Glucose Homeostasis in Mice and Monkeys," The Journal of Pharmacology and Experimental Therapeutics, 2009, pp. 102-111, vol. 329, No. 1, The American Society for Pharmacology and Experimental Therapeutics, U.S.A.
J. Buggy, et al., "Human Glucagon Receptor Monoclonal Antibodies: Antagonism of Glucagon Action and Use in Receptor Characterization," Horm Metab Res, 1996, pp. 215-219, vol. 28, No. 5, Connecticut, U.S.A.
Wei Gu, et al., "Long-Term Inhibition of the Glucagon Receptor with a Monoclonal Antibody in Mice Causes Sustained Improvement in Glycemic Control, with Reversible a-Cell Hyperplasia and Hyperglucagonemia," The Journal of Pharmacology and Experimental Therapeutics, 2009, pp. 871-881, vol. 331, No. 3, The American Society for Pharmacology and Experimental Therapeutics, U.S.A.

* cited by examiner

*Primary Examiner* — Elizabeth C Kemmerer
*Assistant Examiner* — Regina M Deberry
(74) *Attorney, Agent, or Firm* — Cantor Colburn LLP

(57) ABSTRACT

Disclosed are immunological compositions and methods for reducing activity of glucagon signaling using antibodies against glucagon receptor.

4 Claims, 7 Drawing Sheets

Fig. 3
SEQ ID No. 2 – HC1

EVQLLESGGGLVQPGGSLRLSCAASGFTFSSYAMSWVRQAPGKGLEWVSAISGSGGSTYYADSVKGRFTISR
DNSKNTLYLQMNSLRAEDTAVYYCAADSRTQYYDFWSGYYGSGMDVWGQGTLVTVSS

SEQ ID No. 4 – HC 2
HC2EVQLVQSGAEVKKPGSSLKVSCKASGGTFSNNVAISWVRQAPGEGLEWMGGIIPMFGTANYAQKFQG
RVTITADKSTNTAYMELSSLTSDDTAVYYCAREDLTSCAGGGCYPGDWYFDLWGRGTLVTVSS

SEQ ID No. 6 – HC3

EVQLLESGGGLVQPGGSLRLSCAASGFTFSWYQMTWVRQAPGKGLEWVSSIYSSGGITLYADSVKGRFTISR
DNSKNTLYLQMNSLRAEDTAVYYCAKDYGPFGVVPDAFDIWGQGTMVTVSS

SEQ ID No. 8 – HC4

EVQLVQSGAEVKKSGSSVKVSCKASGDTFNTYAINWVRQAPGQGLEWMGGVIPIFPITDYAQNFQGRVTIT
ADESTSTAYMELNSLTSEDTAVYFCAAGDWGGPIAKPHYFDYWGQGTMVTVSS

SEQ ID No.10 – HC5

EVQLVQSGAEVKKPGSSVKVSCKASGGSFSYYTMSWVRQAPGQGLEWMGGIIPIYGPPNYAQKFQGRVTIT
ADESTSTAYMELTSLRSEDTAVYYCATKAPPPTYFDYMDVWGKGTMVTVSS

SEQ ID No. 12 – HC6

EVQLLESGGGLVQPGGSLRLSCAASGFTFSSNAMSWVRQAPGKGLEWVSAISQKGNSTYYADSVKGRFTISR
DNSKNTLYLQMNSLRAEDTAVYYCAREGFWFMPDTEFDYWGQGTLVTVSS

Fig. 4

SEQ ID No. 14 – HC7

EVQLLESGGGLVQPGGSLRLSCAASGFTFSSYAMSWVRQAPGKGLEWVSAISGSGGSTYYADSVKGRFTISR
DNSKNTLYLQMNSLRAEDTAVYYCAREGSWFMPDTEFDYWGQGTLVTVSS

SEQ ID No. 16 – HC8

EVQLLESGGGLVQPGGSLRLSCAASGFTFSSNAMSWVRQAPGKGLEWVSGTSQKGNRTYYADSVKHRFTIS
RDNSKNTLYLQMNSLRAEDTAVYYCAREGFWFMPDTEFDYWGQGTLVTVSS

SEQ ID No. 18 – LC1

HVILTQPPSVSAAPRQRVTISCSGSSSNIRDNAVTWYQQVPGKAPKLLIYSDDLLPSGVSDRFSGSKSGTSASL
AISGLQSEDEADYYCAAWDDRLNGVVFGGGTKVTVL

SEQ ID No. 20 – LC2

QSVVTQPPSASGTPGQRVTISCSGGISDIGSNTVNWYQQVPGTAPKVLIYFDDRRPSGVPDRFSGYKSGTSAS
LAISGLQSEDEADYYCATWDDSLNGPVFGGGTKLTVL

SEQ ID No. 22 – LC3
QAVLTQPSSVSGAPGQRVTISCTGSSSNVGSIYGVHWYQQVPGAAPKLLIYDHSNRPSGVPDRFSGSTSGTS
ASLTISGLQAEDEADYYCQSYDSSLSGSGVFGTGTKVTVL

SEQ ID No. 24 – LC4

QAVLTQPSSVSGAPGQRVTVSCTGTSSNIGAGYDVHWYQQLPGVAPKLVIFGNTYRPSGVPDRFSGSKSDTS
ASLAITGLQPDDEAEYFCQSYDNRLSAWVFGGGTKLTVL

Fig. 5

SEQ ID No. 26 – LC5

QSVLTQPPSVSGAPGQRVTISC<u>TGSSSNIGAGFDVH</u>WYQQLPGTAPKLLIY<u>GNDYRPS</u>GVPDRFSGSKSGTS
ASLAITGLQAEDEADYYC<u>QSFDSSLATRIV</u>GFGGGTKLTVL

SEQ ID No. 28 – LC6

QSVLTQPPSVSGAPGQRVTISC<u>TGSSSNIGAGFDVH</u>WYQQLPGTAPKLLIY<u>GNDYRPS</u>GVPDRFSGSKSGTS
ASLAITGLQAEDEADYYC<u>QSFDSSLVTMNHV</u>FGGGTKLTVL

SEQ ID No. 30 – LC7

QSVLTQPPSVSGAPGQRVTISC<u>TGSSSNIGAGFDVH</u>WYQQLPGTAPKLLIY<u>GNTYRPS</u>GVPDRFSGSKSGTSA
SLAITGLQAEDEADYYC<u>QSFDSSLSGRDVL</u>FGGGTKLTVL

SEQUENCE LISTING

<160> NUMBER OF SEQ ID NOS: 30

<210> SEQ ID NO 1
<211> LENGTH: 387
<212> TYPE: DNA
<213> ORGANISM: Homo sapiens

<400> SEQUENCE: 1

```
gaggtgcagc tgttggagtc tgggggaggc ttggtacagc ctgggggtc cctgagactc      60 tcctgtgcag cctctggatt caccttagc agctatgcca tgagctgggt ccgccaggct     120
ccagggaagg gctggagtg gtctcagct attagtggta gtggtggtag cacatactac     180
gcagactccg tgaagggccg gttcaccatc tccagagaca attccaagaa cacgctgtat    240
ctgcaaatga acagcctgag agccgaggac acggccgtgt attactgtgc ggcagattca    300
aggacccagt actacgattt ctggagtggt tattatggta gcggtatgga cgtctggggc    360
caaggaaccc tggtcaccgt ctctagt                                        387
```

<210> SEQ ID NO 2
<211> LENGTH: 129
<212> TYPE: PRT
<213> ORGANISM: Homo sapiens

<400> SEQUENCE: 2

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Ser Arg Thr Gln Tyr Tyr Asp Phe Trp Ser Gly Tyr Tyr
            100                 105                 110
```

```
Gly Ser Gly Met Asp Val Trp Gly Gln Gly Thr Leu Val Thr Val Ser
            115                 120                 125

Ser
```

<210> SEQ ID NO 3
<211> LENGTH: 390
<212> TYPE: DNA
<213> ORGANISM: Homo sapiens

<400> SEQUENCE: 3

```
gaggtccagc tggtgcagtc tggggctgag gtgaagaagc ctgggtcctc gctgaaggtc      60
tcctgcaagg cttctggagg caccttcagc aataatgtag ccatcagctg ggtgcgacag     120
gccccaggag aagggcttga gtggatgggc gggatcatcc ctatgtttgg tacggccaac     180
tacgcacaga aatttcaggg cagagtcacc attaccgcgg acaaatcaac gaacacagcc     240
tacatggagt tgagcagtct gacatctgac gacacggccg tatattattg cgagagaa      300
gacttaaccc tcatgtgctgg tggtggttgc tacccggggg actggtactt cgatctctgg     360
ggcaggggaa ccctggtcac cgtctctagt                                       390
```

<210> SEQ ID NO 4
<211> LENGTH: 130
<212> TYPE: PRT
<213> ORGANISM: Homo sapiens

<400> SEQUENCE: 4

```
Glu Val Gln Leu Val Gln Ser Gly Ala Glu Val Lys Lys Pro Gly Ser
  1               5                  10                  15

Ser Leu Lys Val Ser Cys Lys Ala Ser Gly Gly Thr Phe Ser Asn Asn
                 20                  25                  30

Val Ala Ile Ser Trp Val Arg Gln Ala Pro Gly Glu Gly Leu Glu Trp
             35                  40                  45

Met Gly Gly Ile Ile Pro Met Phe Gly Thr Ala Asn Tyr Ala Gln Lys
 50                  55                  60

Phe Gln Gly Arg Val Thr Ile Thr Ala Asp Lys Ser Thr Asn Thr Ala
 65                  70                  75                  80

Tyr Met Glu Leu Ser Ser Leu Thr Ser Asp Asp Thr Ala Val Tyr Tyr
                 85                  90                  95

Cys Ala Arg Glu Asp Leu Thr Ser Cys Ala Gly Gly Cys Tyr Pro
            100                 105                 110

Gly Asp Trp Tyr Phe Asp Leu Trp Gly Arg Gly Thr Leu Val Thr Val
            115                 120                 125

Ser Ser
130
```

<210> SEQ ID NO 5
<211> LENGTH: 369
<212> TYPE: DNA
<213> ORGANISM: Homo sapiens

<400> SEQUENCE: 5

```
gaagttcaat tgttagagtc tggtggcggt cttgttcagc ctggtggttc tttacgtctt      60
tcttgcgctg cttccggatt cactttctct tggtaccaga tgacttgggt tcgccaagct     120
cctggtaaag gtttggagtg gtttcttctc atctattctt ctggtggcat tactctttat     180
gctgactccg ttaaaggtcg cttcactatc tctagagaca actctaagaa tactctctac     240
ttgcagatga acagcttaag ggctgaggac acggccgtgt attactgtgc gaaagattac     300
```

```
ggtcctttg gagtggttcc cgatgctttt gatatctggg gccaagggac aatggtcacc      360
gtctctagt                                                              369
```

<210> SEQ ID NO 6
<211> LENGTH: 123
<212> TYPE: PRT
<213> ORGANISM: Homo sapiens

<400> SEQUENCE: 6

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
            20                  25                  30

Gln Met Thr Trp Val Arg Gln Ala Pro Gly Lys Gly Leu Glu Trp Val
        35                  40                  45

Ser Ser Ile Tyr Ser Ser Gly Gly Ile Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Gly Pro Phe Gly Val Val Pro Asp Ala Phe Asp Ile
            100                 105                 110

Trp Gly Gln Gly Thr Met Val Thr Val Ser Ser
        115                 120
```

<210> SEQ ID NO 7
<211> LENGTH: 372
<212> TYPE: DNA
<213> ORGANISM: Homo sapiens

<400> SEQUENCE: 7

```
gaggtgcagc tggtgcagtc tggggctgag gtgaagaagt ctggggcctc ggtgaaggtc       60
tcctgcaagg cttctggaga caccttcaac acctatgcta tcaactgggt gcgacaggcc      120
cctggccaag actagagtg gatgggaggc gtcatcccta tctttcctat aacagactac       180
gcacagaact tccagggcag agtcacgatt accgcggacg aatccaccag cacagcctac      240
atggaactaa acagcctgaa atctgaggac acggccgttt acttctgtgc agcaggcgat      300
tggggggggc ctatcgccaa acctcactac tttgactact ggggccaggg gacaatggtc      360
accgtctcta gt                                                          372
```

<210> SEQ ID NO 8
<211> LENGTH: 124
<212> TYPE: PRT
<213> ORGANISM: Homo sapiens

<400> SEQUENCE: 8

```
Glu Val Gln Leu Val Gln Ser Gly Ala Glu Val Lys Lys Ser Gly Ser
 1               5                  10                  15

Ser Val Lys Val Ser Cys Lys Ala Ser Gly Asp Thr Phe Asn Thr Tyr
            20                  25                  30

Ala Ile Asn Trp Val Arg Gln Ala Pro Gly Gln Gly Leu Glu Trp Met
        35                  40                  45

Gly Gly Val Ile Pro Ile Phe Pro Ile Thr Asp Tyr Ala Gln Asn Phe
    50                  55                  60
```

Gln Gly Arg Val Thr Ile Thr Ala Asp Glu Ser Thr Ser Thr Ala Tyr
65                  70                  75                  80

Met Glu Leu Asn Ser Leu Thr Ser Glu Asp Thr Ala Val Tyr Phe Cys
                85                  90                  95

Ala Ala Gly Asp Trp Gly Gly Pro Ile Ala Lys Pro His Tyr Phe Asp
            100                 105                 110

Tyr Trp Gly Gln Gly Thr Met Val Thr Val Ser Ser
        115                 120

<210> SEQ ID NO 9
<211> LENGTH: 366
<212> TYPE: DNA
<213> ORGANISM: Homo sapiens

<400> SEQUENCE: 9
gaggtgcagc tggtgcagtc tgggcggaa gtgaagaagc ctggatcctc ggtgaaggtc        60
tcctgcaagg cttctggagg ctccttcagc tactatacga tgagttgggt gcgacaggcc       120
cctggacagg ggcttgagtg gatgggagga atcatcccta tctatggtcc accaaactac       180
gcacagaaat tccagggcag agtcaccatt accgcggacg agtccacgag cacagcctac       240
atggagctga ccagcctgag atctgaagac acggccgtgt attattgtgc gacaaaggcc       300 ccccgccta cctacttcga ctacatggac gtctggggca agggacaat ggtcaccgtc        360 tctagt                                                                 366

<210> SEQ ID NO 10
<211> LENGTH: 122
<212> TYPE: PRT
<213> ORGANISM: Homo sapiens

<400> SEQUENCE: 10

Glu Val Gln Leu Val Gln Ser Gly Ala Glu Val Lys Lys Pro Gly Ser
1               5                   10                  15

Ser Val Lys Val Ser Cys Lys Ala Ser Gly Gly Ser Phe Ser Tyr Tyr
            20                  25                  30

Thr Met Ser Trp Val Arg Gln Ala Pro Gly Gln Gly Leu Glu Trp Met
        35                  40                  45

Gly Gly Ile Ile Pro Ile Tyr Gly Pro Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Thr Ser Leu Arg Ser Glu Asp Thr Ala Val Tyr Tyr Cys
                85                  90                  95

Ala Thr Lys Ala Pro Pro Pro Thr Tyr Phe Asp Tyr Met Asp Val Trp
            100                 105                 110

Gly Lys Gly Thr Met Val Thr Val Ser Ser
        115                 120

<210> SEQ ID NO 11
<211> LENGTH: 366
<212> TYPE: DNA
<213> ORGANISM: Homo sapiens

<400> SEQUENCE: 11
gaggtgcagc tgttggagtc tgggggaggc ttggtacagc ctggggggtc cctgagactc        60
tcctgtgcag cctctggatt cacctttagc agcaatgcca tgagctgggt ccgccaggcg       120
ccagggaagg ggctggagtg ggtctcagct attagtcaga agggtaatag cacatactac       180

```
gcagactccg tgaagggccg gttcaccatc tccagagaca attccaagaa cacgctgtat    240
ctgcaaatga acagcctgag agccgaggac acggccgtgt attactgtgc gagagaaggg    300
ttttggttta tgcctgacac cgagtttgac tactggggcc aaggcaccct ggtcaccgtc    360
tctagt                                                               366
```

<210> SEQ ID NO 12
<211> LENGTH: 122
<212> TYPE: PRT
<213> ORGANISM: Homo sapiens

<400> SEQUENCE: 12

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Asn
             20                  25                  30

Ala Met Ser Trp Val Arg Gln Ala Pro Gly Lys Gly Leu Glu Trp Val
         35                  40                  45

Ser Ala Ile Ser Gln Lys Gly Asn Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Phe Trp Phe Met Pro Asp Thr Glu Phe Asp Tyr Trp
            100                 105                 110

Gly Gln Gly Thr Leu Val Thr Val Ser Ser
        115                 120
```

<210> SEQ ID NO 13
<211> LENGTH: 367
<212> TYPE: DNA
<213> ORGANISM: Homo sapiens

<400> SEQUENCE: 13

```
gaggtgcagc tgttggagtc tgggggaggc ttggtacagc ctggggggtc cctgagactc     60
tcctgtgcag cctctggatt cacctttagc agctatgcca tgagctgggt ccgccaggcg    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gagagaaggg    300
tcgtggttta tgcctgacac cgagtttgac tactggggcc agggcaccct ggtcaccgtc    360
ttctagt                                                              367
```

<210> SEQ ID NO 14
<211> LENGTH: 122
<212> TYPE: PRT
<213> ORGANISM: Homo sapiens

<400> SEQUENCE: 14

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45
```

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ser Trp Phe Met Pro Asp Thr Glu Phe Asp Tyr Trp
            100                 105                 110

Gly Gln Gly Thr Leu Val Thr Val Ser Ser
        115                 120

<210> SEQ ID NO 15
<211> LENGTH: 366
<212> TYPE: DNA
<213> ORGANISM: Homo sapiens

<400> SEQUENCE: 15

| | | | | | |
|---|---|---|---|---|---|
| gaggtgcagc | tgttggagtc | tgggggaggc | ttggtacagc | ctgggggtc | cctgagactc | 60 |
| tcctgtgcag | cctctggatt | cacctttagc | agcaatgcca | tgagctgggt | ccgccaggcg | 120 |
| ccagggaagg | ggctggagtg | ggtctcaggc | accagtcaga | aaggcaaccg | tacatactac | 180 |
| gcagactccg | tgaagcaccg | gttcaccatc | tccagagaca | attccaagaa | cacgctgtat | 240 |
| ctgcaaatga | acagcctgag | agccgaggac | acggccgtgt | attactgtgc | gagagaaggg | 300 |
| ttttggttta | tgcctgacac | cgagtttgac | tactggggcc | aaggcaccct | ggtcaccgtc | 360 |
| tctagt | | | | | | 366 |

<210> SEQ ID NO 16
<211> LENGTH: 122
<212> TYPE: PRT
<213> ORGANISM: Homo sapiens

<400> SEQUENCE: 16

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Asn
                 20                  25                  30

Ala Met Ser Trp Val Arg Gln Ala Pro Gly Lys Gly Leu Glu Trp Val
             35                  40                  45

Ser Gly Thr Ser Gln Lys Gly Asn Arg Thr Tyr Tyr Ala Asp Ser Val
         50                  55                  60

Lys His Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Phe Trp Phe Met Pro Asp Thr Glu Phe Asp Tyr Trp
            100                 105                 110

Gly Gln Gly Thr Leu Val Thr Val Ser Ser
        115                 120

<210> SEQ ID NO 17
<211> LENGTH: 330
<212> TYPE: DNA
<213> ORGANISM: Homo sapiens

<400> SEQUENCE: 17

```
cacgttatac tgactcaacc gccctcggtg tctgcagccc ccaggcagcg ggtcaccatc    60
tcctgttctg gaagcagctc caacattcga gataatgctg taacctggta ccagcaggtc   120
ccgggaaagg ctcccaaact cctcatctat tctgatgatc tgctgccctc aggggtctct   180
gaccgattct ctggctccaa gtctggcacc tcagcctccc tggccatcag tgggctccag   240
tctgaggatg aggctgatta ttactgtgca gcatgggatg acaggctgaa tggtgtcgtc   300
ttcggcggag ggaccaaggt caccgtccta                                    330
```

<210> SEQ ID NO 18
<211> LENGTH: 110
<212> TYPE: PRT
<213> ORGANISM: Homo sapiens

<400> SEQUENCE: 18

```
His Val Ile Leu Thr Gln Pro Pro Ser Val Ser Ala Ala Pro Arg Gln
  1               5                  10                  15
Arg Val Thr Ile Ser Cys Ser Gly Ser Ser Asn Ile Arg Asp Asn
             20                  25                  30
Ala Val Thr Trp Tyr Gln Gln Val Pro Gly Lys Ala Pro Lys Leu Leu
         35                  40                  45
Ile Tyr Ser Asp Asp Leu Leu Pro Ser Gly Val Ser Asp Arg Phe Ser
     50                  55                  60
Gly Ser Lys Ser Gly Thr Ser Ala Ser Leu Ala Ile Ser Gly Leu Gln
 65                  70                  75                  80
Ser Glu Asp Glu Ala Asp Tyr Tyr Cys Ala Ala Trp Asp Asp Arg Leu
                 85                  90                  95
Asn Gly Val Val Phe Gly Gly Gly Thr Lys Val Thr Val Leu
            100                 105                 110
```

<210> SEQ ID NO 19
<211> LENGTH: 330
<212> TYPE: DNA
<213> ORGANISM: Homo sapiens

<400> SEQUENCE: 19

```
cagtctgtcg tgacgcagcc gccctcagca tctgggactc ccgggcagag ggtcaccatc    60
tcttgctctg gaggcatctc cgacatcgga agtaatactg tcaattggta tcagcaagtc   120
ccaggaacgg cccccaaagt cctcatctat tttgatgatc ggcggccctc agggatccct   180
gaccgattct ctgggtacaa gtctggcacg tcagcctccc tggccatcag tgggctccag   240
tctgaggatg aggctgatta ttattgtgca acatgggatg acagcctgaa tggtccggtg   300
ttcggcggag ggaccaagct gaccgtccta                                    330
```

<210> SEQ ID NO 20
<211> LENGTH: 110
<212> TYPE: PRT
<213> ORGANISM: Homo sapiens

<400> SEQUENCE: 20

```
Gln Ser Val Val Thr Gln Pro Pro Ser Ala Ser Gly Thr Pro Gly Gln
  1               5                  10                  15
Arg Val Thr Ile Ser Cys Ser Gly Gly Ile Ser Asp Ile Gly Ser Asn
             20                  25                  30
Thr Val Asn Trp Tyr Gln Gln Val Pro Gly Thr Ala Pro Lys Val Leu
         35                  40                  45
```

```
Ile Tyr Phe Asp Asp Arg Arg Pro Ser Gly Val Pro Asp Arg Phe Ser
         50                  55                  60

Gly Tyr Lys Ser Gly Thr Ser Ala Ser Leu Ala Ile Ser Gly Leu Gln
 65                  70                  75                  80

Ser Glu Asp Glu Ala Asp Tyr Tyr Cys Ala Thr Trp Asp Asp Ser Leu
                 85                  90                  95

Asn Gly Pro Val Phe Gly Gly Gly Thr Lys Leu Thr Val Leu
            100                 105                 110

<210> SEQ ID NO 21
<211> LENGTH: 336
<212> TYPE: DNA
<213> ORGANISM: Homo sapiens

<400> SEQUENCE: 21
caggctgtgc tgactcagcc gtcctcagtg tctggggccc cagggcagag ggtcaccatc      60
tcctgcactg ggagcagctc caacgtcggg tcaatttatg gtgttcactg gtaccagcag     120
gttccaggag ccgcccccaa actcctcatc tatgatcact ccaatcggcc ctcaggggtc     180
cctgaccgat tctctggctc cacgtctggc acctcagcct ccctgaccat ctctgggctc     240
caggctgagg atgaggctga ttattactgc cagtcctacg acagcagcct gagtggttcg     300
ggagtcttcg gaactgggac caaggtcacc gtccta                               336

<210> SEQ ID NO 22
<211> LENGTH: 112
<212> TYPE: PRT
<213> ORGANISM: Homo sapiens

<400> SEQUENCE: 22

Gln Ala Val Leu Thr Gln Pro Ser Ser Val Ser Gly Ala Pro Gly Gln
  1               5                  10                  15

Arg Val Thr Ile Ser Cys Thr Gly Ser Ser Ser Asn Val Gly Ser Ile
             20                  25                  30

Tyr Gly Val His Trp Tyr Gln Gln Val Pro Gly Ala Ala Pro Lys Leu
         35                  40                  45

Leu Ile Tyr Asp His Ser Asn Arg Pro Ser Gly Val Pro Asp Arg Phe
     50                  55                  60

Ser Gly Ser Thr Ser Gly Thr Ser Ala Ser Leu Thr Ile Ser Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Ser Gly Val Phe Gly Thr Gly Thr Lys Val Thr Val Leu
            100                 105                 110

<210> SEQ ID NO 23
<211> LENGTH: 333
<212> TYPE: DNA
<213> ORGANISM: Homo sapiens

<400> SEQUENCE: 23
caggctgtgc tgactcagcc gtcctcagtg tctggggccc cagggcagag ggtcaccgtc      60
tcctgcactg ggaccagctc caacatcggg gcaggttatg atgtacactg gtaccagcaa     120
cttccaggag tggccccaaa actcgtcatc tttggtaaca cttatcggcc ctcaggggtc     180
cctgaccgat tctctggctc caagtctgac acctcagcct ccctggccat cactggtctc     240
```

```
cagcctgacg atgaggctga gtatttctgc cagtcctatg acaacagact gagtgcttgg      300
gtgttcggcg agggaccaa gctgaccgtc cta                                    333
```

<210> SEQ ID NO 24
<211> LENGTH: 111
<212> TYPE: PRT
<213> ORGANISM: Homo sapiens

<400> SEQUENCE: 24

```
Gln Ala Val Leu Thr Gln Pro Ser Ser Val Ser Gly Ala Pro Gly Gln
  1               5                  10                  15

Arg Val Thr Val Ser Cys Thr Gly Thr Ser Ser Asn Ile Gly Ala Gly
             20                  25                  30

Tyr Asp Val His Trp Tyr Gln Gln Leu Pro Gly Val Ala Pro Lys Leu
         35                  40                  45

Val Ile Phe Gly Asn Thr Tyr Arg Pro Ser Gly Val Pro Asp Arg Phe
     50                  55                  60

Ser Gly Ser Lys Ser Asp Thr Ala Ser Leu Ala Ile Thr Gly Leu
 65                  70                  75                  80

Gln Pro Asp Asp Glu Ala Glu Tyr Phe Cys Gln Ser Tyr Asp Asn Arg
                 85                  90                  95

Leu Ser Ala Trp Val Phe Gly Gly Gly Thr Lys Leu Thr Val Leu
            100                 105                 110
```

<210> SEQ ID NO 25
<211> LENGTH: 339
<212> TYPE: DNA
<213> ORGANISM: Homo sapiens

<400> SEQUENCE: 25

```
cagtctgtgc tgacgcagcc gccctcagtg tctggggccc ccgggcagag ggtcaccatc       60
tcctgcactg ggagcagttc caacatcggg gctggctttg atgtgcactg gtaccagcag      120
cttccaggaa cagcccccaa actcctcatc tatgggaacg actatcgacc ctcaggagtc      180
cctgaccgat tctctggctc caagtctggc acctcagcct ccctggccat cactggcctc      240
caggctgagg atgaggctga ttattactgc cagtcctttg actcgagcct agcgacgcgg      300
attgtggggt tcggcggagg gaccaagctg accgtccta                             339
```

<210> SEQ ID NO 26
<211> LENGTH: 113
<212> TYPE: PRT
<213> ORGANISM: Homo sapiens

<400> SEQUENCE: 26

```
Gln Ser Val Leu Thr Gln Pro Pro Ser Val Ser Gly Ala Pro Gly Gln
  1               5                  10                  15

Arg Val Thr Ile Ser Cys Thr Gly Ser Ser Ser Asn Ile Gly Ala Gly
             20                  25                  30

Phe Asp Val His Trp Tyr Gln Gln Leu Pro Gly Thr Ala Pro Lys Leu
         35                  40                  45

Leu Ile Tyr Gly Asn Asp Tyr Arg Pro Ser Gly Val Pro Asp Arg Phe
     50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Phe Asp Ser Ser
                 85                  90                  95
```

Leu Ala Thr Arg Ile Val Gly Phe Gly Gly Gly Thr Lys Leu Thr Val
                100                 105                 110

Leu

<210> SEQ ID NO 27
<211> LENGTH: 339
<212> TYPE: DNA
<213> ORGANISM: Homo sapiens

<400> SEQUENCE: 27
cagtctgtgc tgacgcagcc gccctcagtg tctggggccc ccgggcagag ggtcaccatc        60
tcctgcactg ggagcagttc aacatcgggg gctggctttg atgtgcactg gtaccagcag       120
cttccaggaa cagcccccaa actcctcatc tatgggaacg actatcgacc ctcaggagtc       180
cctgaccgat tctctggctc caagtctggc acctcagcct ccctggccat cactggcctc       240
caggctgagg atgaggctga ttattactgc cagtcctttg actcgagcct agtgacgatg       300
aatcatgtgt tcggcggagg gaccaagctg accgtccta                              339

<210> SEQ ID NO 28
<211> LENGTH: 113
<212> TYPE: PRT
<213> ORGANISM: Homo sapiens

<400> SEQUENCE: 28

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
                 20                  25                  30

Phe Asp Val His Trp Tyr Gln Gln Leu Pro Gly Thr Ala Pro Lys Leu
             35                  40                  45

Leu Ile Tyr Gly Asn Asp Tyr Arg Pro Ser Gly Val Pro Asp Arg Phe
     50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Phe Asp Ser Ser
                 85                  90                  95

Leu Val Thr Met Asn His Val Phe Gly Gly Gly Thr Lys Leu Thr Val
                100                 105                 110

Leu

<210> SEQ ID NO 29
<211> LENGTH: 339
<212> TYPE: DNA
<213> ORGANISM: Homo sapiens

<400> SEQUENCE: 29
cagtctgtgt tgacgcagcc gccctcagtg tctggggccc ccgggcagag ggtcaccatc        60
tcctgcactg ggagcagttc aacatcgggg gctggctttg atgtgcactg gtaccagcag       120
cttccaggaa cagcccccaa actcctcatc tatgggaaca cctatcgacc ctcaggagtc       180
cctgaccgat tctctggctc caagtctggc acctcagcct ccctggccat cactggcctc       240
caggctgagg atgaggctga ttattactgc cagtcctttg acagcagcct aagtggccgg       300
gatgtgctat tcggcggagg gaccaagctg accgtccta                              339

```
<210> SEQ ID NO 30
<211> LENGTH: 113
<212> TYPE: PRT
<213> ORGANISM: Homo sapiens

<400> SEQUENCE: 30

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
                20                  25                  30

Phe Asp Val His Trp Tyr Gln Gln Leu Pro Gly Thr Ala Pro Lys Leu
            35                  40                  45

Leu Ile Tyr Gly Asn Thr Tyr Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Phe Asp Ser Ser
                85                  90                  95

Leu Ser Gly Arg Asp Val Leu Phe Gly Gly Gly Thr Lys Leu Thr Val
                100                 105                 110

Leu
```

ANTIBODIES AGAINST GLUCAGON RECEPTOR AND THEIR USE

TECHNICAL FIELD

The present invention relates to the compositions and methods related to antibodies against glucagon receptor and derivatives of these antibodies. The invention further concerns pharmaceutical compositions and derivatives useful in such methods. More specifically, the invention relates to the production, diagnostic use, and therapeutic use of monoclonal and polyclonal antibodies, and fragments thereof, which specifically bind to glucagon receptor.

BACKGROUND ART

Fasting hyperglycemia in patients with poorly controlled type II diabetes mellitus is closely associated with increased rates of glucose production which in turn can be ascribed to increased rates of gluconeogenesis. A number of studies have demonstrated that elevated glucagon level is partially responsible for the increased hepatic glucose production in patients with type 2 diabetes.

Glucagon is a 29-amino-acid hormone in the pancreatic alpha cells, which plays a major counter-regulatory role for insulin action. During fasting, glucagon secretion increases in response to the low circulating glucose levels. Increased glucagon secretion stimulates glucose production by promoting hepatic gluconeogenesis and glycogenolysis. In addition, glucagon reduces glycogen synthesis in the liver. Clinically, glucagon is administered to patients who are at risk for significant hypoglycemia. Conversely, inhibition of the glucagon pathway may offer a strategy for the treatment of type II diabetes.

The biological effects of glucagon are mediated through its binding to a specific receptor on cell surface, glucagon receptor, and subsequent activation of the signaling pathway. The glucagon receptor belongs to the family B G-protein coupled receptor (GPCR). It is predominantly expressed in liver and kidney, which reflects its primary role as a regulator of glucose output and gluconeogenesis in these tissues. The activation of glucagon receptor in the liver stimulates adenylyl cyclase activity and phosphoinositol turnover, resulting in increased expression of several key gluconeogenic enzymes.

Considering the key role of glucagon in control of hyperglycemia, strategy for inhibiting glucagon activation pathway can provide a therapeutic means to treat type II diabetes.

DISCLOSURE OF INVENTION

Technical Problem

The object of present invention is to provide antibodies against glucagon receptor.

Another object of the present invention is to provide recombinant vectors, host cells, isolated cell lines, and hybridomas for the production of such antibodies.

It is still another object of the present invention to provide pharmaceutical compositions containing the antibodies.

It is still another object of the present invention to provide methods for treating type II diabetes and related disease using these antibodies.

Solution to Problem

One aspect of the present invention relates to isolated antibodies, or antigen-binding portions or derivatives thereof, that specifically bind to glucagon receptor.

In one embodiment, the present invention provides an isolated antibody, or an antigen-binding portion or a derivative thereof, comprising:

(a) a first CDR set, CDR1, CDR2 and CDR3, that sequentially together comprise the amino acid sequences of heavy chain CDRs, CDR1, CDR2 and CDR3, sequentially together, that are included in the amino acid sequence as set forth in any one of SEQ ID Nos. 2, 4, 6, 8, 10, 12, 14, and 16;

(b) a second CDR set, CDR1, CDR2 and CDR3, that sequentially together comprises the amino acid sequences of light chain CDRs, CDR1, CDR2 and CDR3, sequentially together, that are included in the amino acid sequence set forth in any one of SEQ ID Nos. 18, 20, 22, 24, 26, 28 and 30; or, (c) a combination of the first CDR set of (a) and the second CDR set of (b).

In a preferable embodiment, the antibody comprises a heavy chain or a light chain, or both of them, wherein said heavy chain comprises a heavy chain variable region selected from the group consisting of HC1 (SEQ ID No. 2); HC2 (SEQ ID No. 4); HC3 (SEQ ID No. 6); HC4 (SEQ ID No. 8); HC5 (SEQ ID No. 10); HC6 (SEQ ID No. 12); HC7 (SEQ ID No. 14); HC8 (SEQ ID No. 16); and antigen-binding fragments thereof; and said light chain comprises a light chain variable region selected from the group consisting of: LC1 (SEQ ID No. 18); LC2 (SEQ ID No. 20); LC3 (SEQ ID No. 22); LC4 (SEQ ID No. 24); LC5 (SEQ ID No. 26); LC6 (SEQ ID No. 28); LC7 (SEQ ID No. 30); and antigen-binding fragments thereof.

In a more preferable embodiment, the antibody of the present invention is selected from the group consisting of:

(a) an antibody comprising the amino acid sequences as set forth in SEQ ID No. 2 and SEQ ID No. 18 (Ab1);

(b) an antibody comprising the amino acid sequences as set forth in SEQ ID No. 4 and SEQ ID No. 20 (Ab2);

(c) an antibody comprising the amino acid sequences as set forth in SEQ ID No. 6 and SEQ ID No. 22 (Ab3);

(d) an antibody comprising the amino acid sequences as set forth in SEQ ID No. 8 and SEQ ID No. 24 (Ab4);

(e) an antibody comprising the amino acid sequences as set forth in SEQ ID No. 6 and SEQ ID No. 26 (Ab5);

(f) an antibody comprising the amino acid sequences as set forth in SEQ ID No. 10 and SEQ ID No. 26 (Ab6);

(g) an antibody comprising the amino acid sequences as set forth in SEQ ID No. 12 and SEQ ID No. 28 (Ab7);

(h) an antibody comprising the amino acid sequences as set forth in SEQ ID No. 14 and SEQ ID No. 30 (Ab8);

(i) an antibody comprising the amino acid sequences as set forth in SEQ ID No. 16 and SEQ ID No. 26 (Ab9); and, (j) an antibody comprising the amino acid sequences as set forth in SEQ ID No. 10 and SEQ ID No. 22 (Ab10).

In another aspect, the present invention relates to an isolated antibody, or an antigen-binding portion or a derivative thereof, which competes for binding to glucagon receptor.

In one embodiment, the isolated antigen binding agent binds to the human glucagon receptor with substantially the same $K_d$ as a reference antibody, or inhibits glucagon stimulation of the receptor with substantially the same $IC_{50}$ of the reference antibody, or competes for binding with the reference antibody.

In another aspect, the present invention relates to an isolated antibody, or an antigen-binding portion or a derivative thereof, comprising:

(a) a first CDR set, CDR1, CDR2 and CDR3, that sequentially together are at least 85% identical in amino acid sequence to heavy chain CDRs, CDR1, CDR2 and CDR3, sequentially together, that are included in the amino acid sequence as set forth in any one of SEQ ID Nos. 2, 4, 6, 8, 10, 12, 14, and 16;

(b) a second CDR set, CDR1, CDR2 and CDR3, that sequentially together are at least 85% identical in amino acid sequence to light chain CDRs, CDR1, CDR2 and CDR3, sequentially together, that are included in the amino acid sequence set forth in any one of SEQ ID Nos. 18, 20, 22, 24, 26, 28 and 30; or, (c) a combination of the first CDR set of (a) and the second CDR set of (b), wherein said antibody, antigen-binding portion or derivative competes for glucagon binding to glucagon receptor.

The antibody may comprise a heavy chain comprising a variable region comprising an amino acid sequence at least 85%, preferably 90%, more preferably 95%, and most preferably 99% identical to the amino acid sequence selected from SEQ ID No. 2, 4, 6, 8, 10, 12, 14 or 16. Further, the antibody may comprise a light chain comprising a variable region comprising an amino acid sequence at least 85%, preferably 90%, more preferably 95%, and most preferably 99% identical to the amino acid sequence selected from SEQ ID No. 18, 20, 22, 24, 26, 28 or 30.

In another aspect, the present invention provides an isolated antibody or an antigen binding portion, comprising an amino acid sequence selected from the group consisting of:

(a) a heavy chain CDR3 sequence that differs by no more than a total of three amino acid additions, deletions, and/or nonconservative substitutions from a CDR3 sequence selected from SEQ ID Nos. 2, 4, 6, 8, 10, 12, 14 and 16;

(b) a light chain CDR3 sequence that differs by no more than a total of three amino acid additions, deletions, and/or nonconservative substitutions from a CDR3 sequence selected from SEQ ID Nos. 18, 20, 22, 24, 26, 28 and 30; or, (c) a combination of a heavy chain CDR3 sequence of (a) and the light chain CDR3 sequence of (b), wherein said antibody or antigen binding portion binds to glucagon receptor.

Another aspect of the present invention relates to a pharmaceutical composition including an antibody or functional fragment thereof, and a pharmaceutically acceptable carrier. Compositions of the invention comprise the heavy and/or light chain, the variable domains thereof, or antigen-binding portions thereof, or nucleic acid molecules encoding the antibody, antibody chain, or variable domain thereof, and a mixture with one or more pharmaceutically acceptable carrier or fusion partner. Compositions of the invention may further comprise another component, such as a therapeutic agent or a diagnostic agent.

Yet another aspect of the present invention relates to an isolated nucleic acid comprising a polynucleotide sequence encoding the light chain variable domain, the heavy chain variable domain, or both, of the antibody. The nucleic acid may comprise the nucleotide sequence as set forth in one or more of SEQ ID Nos. 1, 3, 5, 7, 9, 11, 13, 15, 17, 19, 21, 23, 25, 27 and 29.

A further aspect of the present invention relates to a recombinant expression vector, comprising the nucleic acid of reference sequences.

Still a further aspect of the present invention relates to a host cell transformed with the vector.

Still a further aspect of the present invention relates to an isolated cell line, which produces the antibody, or the heavy chain or light chain or an antigen-binding portion thereof.

Still a further aspect of the present invention relates to a hybridoma producing the antibody, or the heavy chain or light chain or an antigen-binding portion thereof.

Still a further aspect of the present invention relates to a method for lowering blood glucose, improving glucose tolerance, or for treating, preventing or inhibiting type II diabetes, dyslipodemia, or a related disease in a subject in need thereof, comprising the step of administering to the subject the antibody, the antigen-binding portion or the derivative thereof, or the pharmaceutical composition. The glucagon receptor antibodies can be administered alone, or in combination with additional antibodies or other medicines.

Advantageous Effects of Invention

This invention provides compositions and methods based on interfering with glucagon receptor activation, including, but not limited to, by binding to the extracellular portion of glucagon receptor. Antagonists of the invention, as described herein, provide important therapeutic and diagnostic agents for use in targeting pathological conditions associated with diabetes mellitus and related disease. Accordingly, the invention provides methods, compositions, kits, and articles of manufacture related to modulating glucagon receptor pathway.

BRIEF DESCRIPTION OF DRAWINGS

FIGS. 3 to 5 show the predicted amino acid sequences of light and heavy chain variable domains of isolated anti-glucagon receptor antibodies. The underlined sequences represent, from left to right, the CDR1, CDR2, and CDR3.

Mode for the Invention

Definitions

Figure 1:
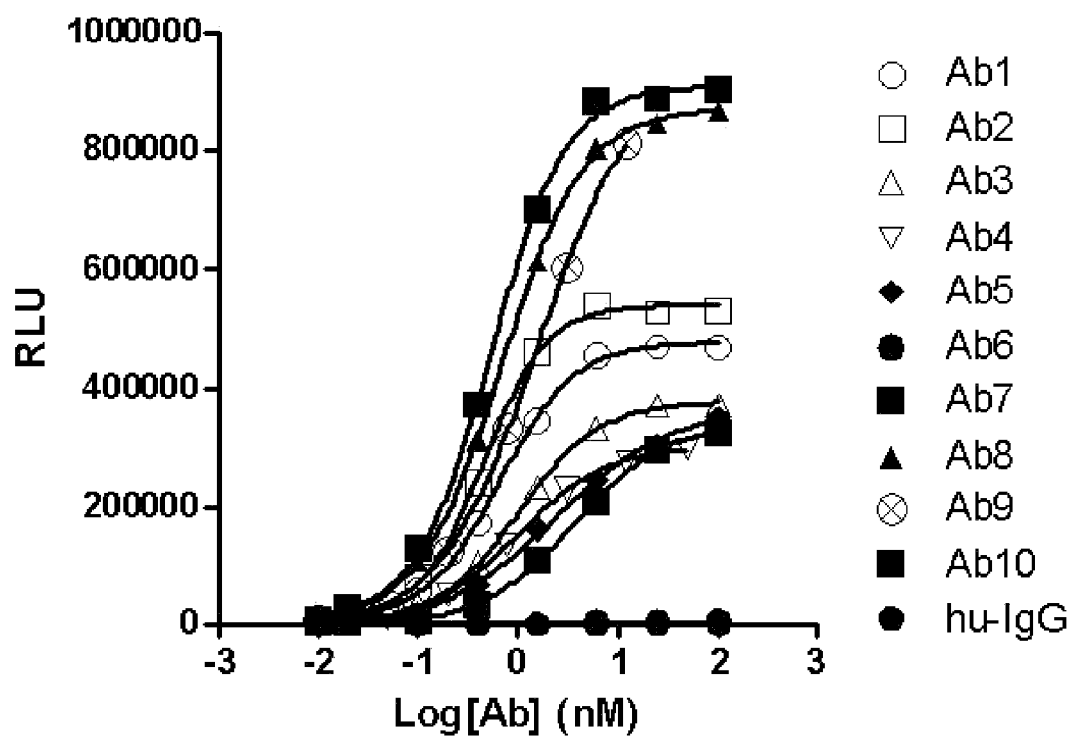
FIG. 1 is a graphical representation showing the ability of selected antibodies binding to the glucagon receptor that is expressed on cell surface. Varying amounts of antibodies were added to the CHO cells expressing the full length human glucagon receptor. After washing, antibodies remained to the cells were detected by HRP conjugated anti-human antibody followed by substrate addition for HRP activity.
Figure 2:
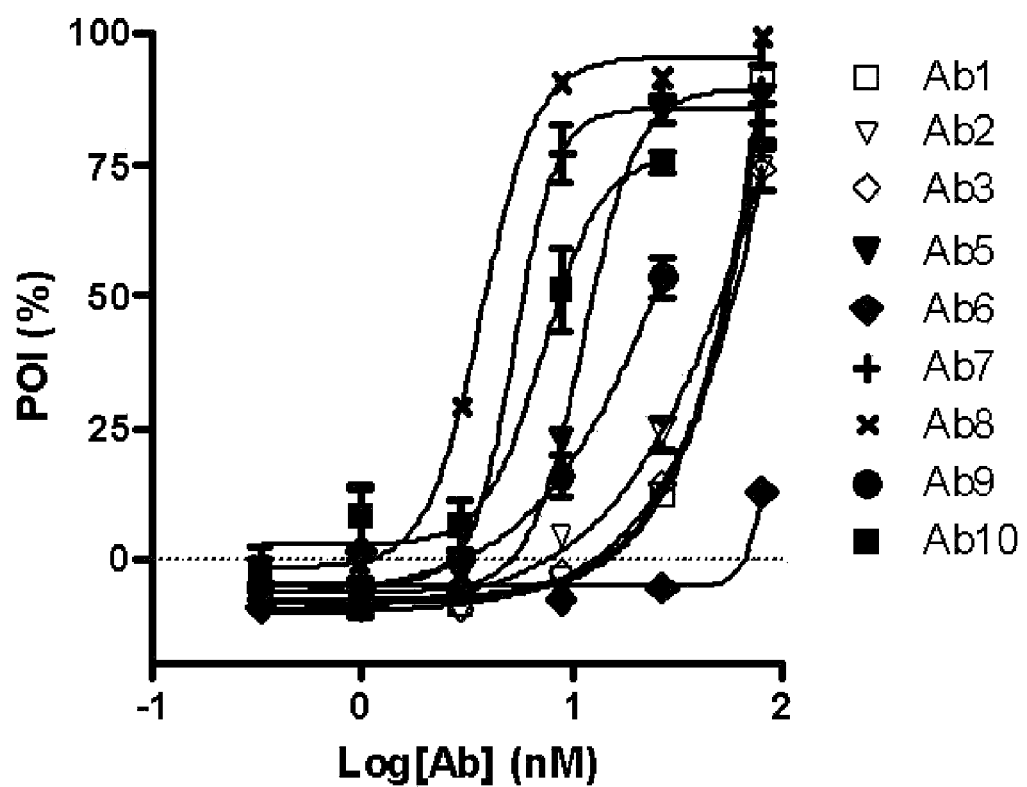
FIG. 2 shows a graph illustrating inhibition of cAMP production by antibodies against glucagon receptor upon glucagon stimulation. A stable cell line expressing full length human glucagon receptor was incubated with varying amounts of antibodies. After 15 min, 100 pM of glucagon was added to the cells and level of cAMP was measured using cAMP HTRF kit (CIS Bio). The average values and standard deviation from duplicate samples are shown.
Figure 6:
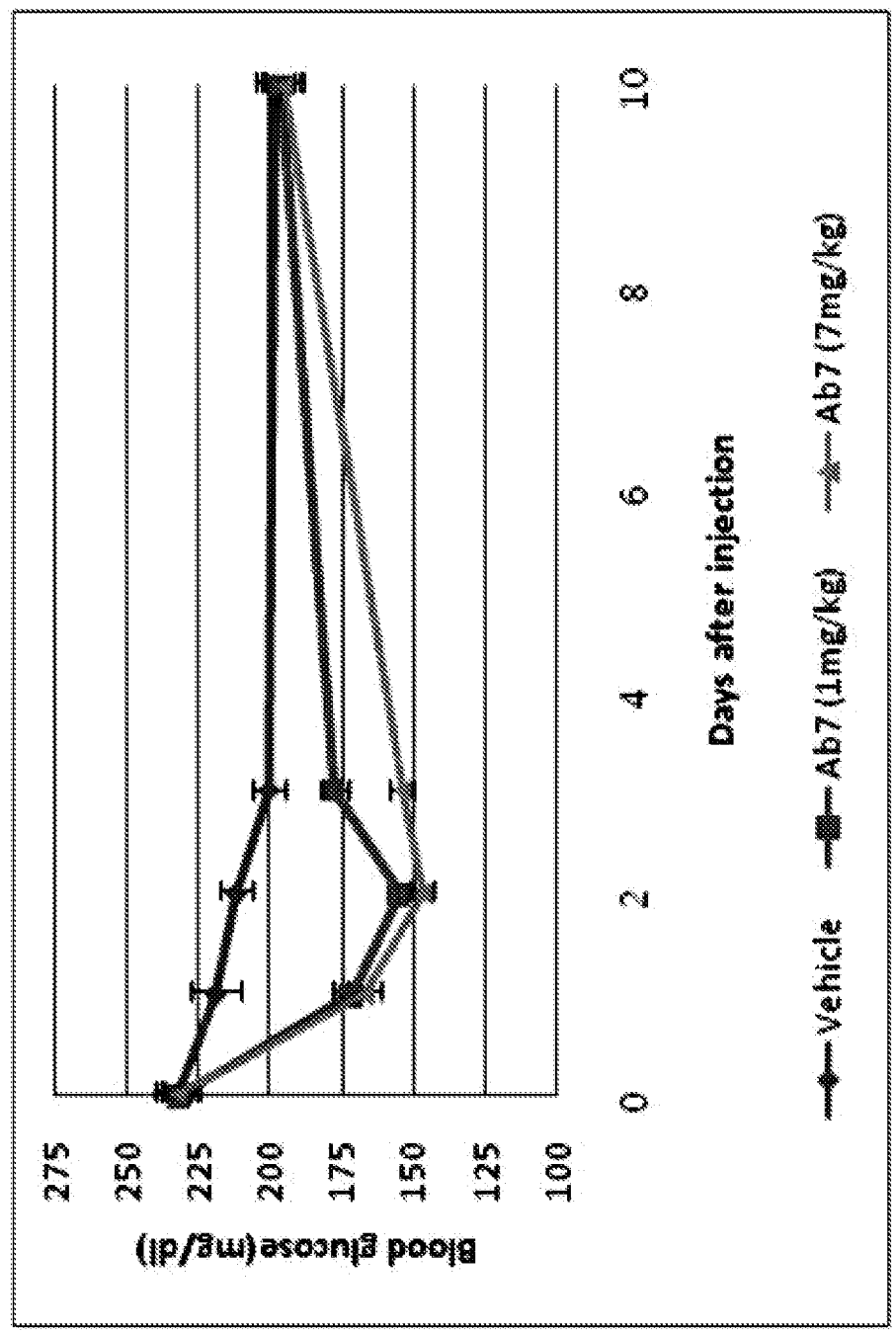
FIG. 6 shows the blood glucose level in high fat induced obese mice injected with the selected antibody (Ab7) at 1 mg/kg and 7 mg/kg. Blood glucose was measured at day 0, 1, 2, 3, and 10 after single injection of either antibody or buffer control. The values are calculated average and standard deviation from nine to ten mice in each group.
Figure 7:
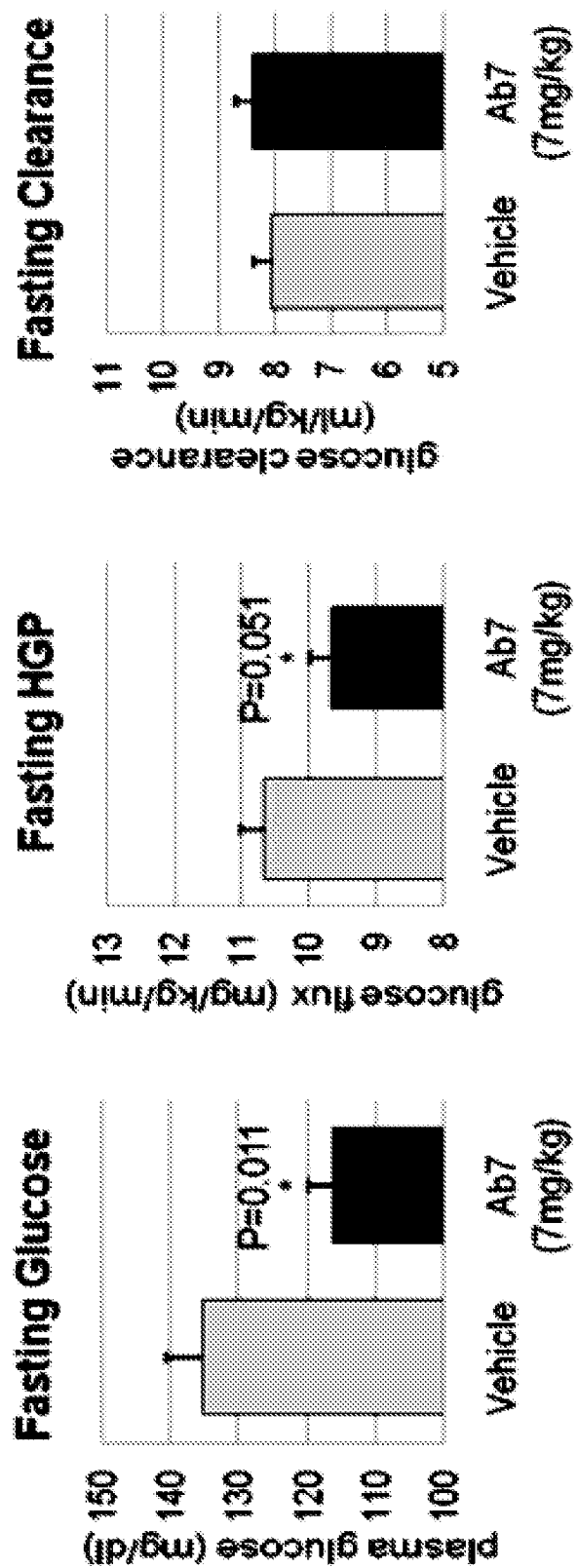
FIG. 7 represents the graphical view of fasting plasma glucose levels and basal rates of hepatic glucose production (HGP) in high fat induced obese mice. Basal HGP was determined by radioisotope dilution method (Choi C. S. et al, *Proc Natl Acad Sci U-S-A*, 2007, 104:16480-85). Fasting plasma glucose levels and basal HGP rates were significantly decreased in mice injected with 7 mg/kg of Ab7, compared with vehicle injected group, while basal glucose clearance rates was not different between two groups. Data are expressed as mean values+/−SEM for 10 mice per group.

The term, 'an antibody,' as used herein, means a protein consisting of one or more polypeptides substantially encoded by all or part of the recognized immunoglobulin genes. The recognized immunoglobulin genes, for example in humans, include the kappa, lambda, and heavy chain genetic loci, which together comprise the myriad variable region genes, and the constant region genes. Herein, 'antibody' may mean 'a specific antigen binding agent.' A skilled person in the art would readily appreciate that the antibody can be used as a therapeutic or diagnostic agent, and thus, 'antibody' may also be referred to as 'a therapeutic agent' or 'a diagnostic agent.'

An 'isolated antibody,' as used herein, is intended to refer to an antibody that is substantially free of other antibodies having different antigenic specificities (e.g., an isolated antibody that specifically binds glucagon receptor is substantially free of antibodies that specifically bind antigens other than glucagon receptor). An isolated antibody that specifically binds glucagon receptor may, however, have cross-reactivity to other antigens, such as glucagon receptor from other species. Moreover, an isolated antibody may be substantially free of other cellular material and/or chemicals. Further, an isolated antibody, e.g., an isolated human antibody, can be a chimeric antibody wherein, e.g., variable regions, CDR domains, or isotypes derived from a different human source are grafted to the parent human antibody.

The term, 'neutralizing antibody,' for glucagon receptor refers to an antibody that can inhibit a glucagon dependent stimulation of its receptor by about 10~120%, preferably by at least 30, 50, 70, 80, 90, 100% or more, depending on the assay. The capacity of glucagon receptor antibodies to inhibit glucagon signaling is preferably assessed by at least one suitable cell based assay, as described herein and/or as known in the art. One example is to measure the production of cAMP upon stimulation with glucagon, using a kit such as cAMP HTRF kit (CisBio).

The term, 'conservative amino acid substitutions,' as used herein, are substitutions that replace an amino acid residue with one imparting similar or better (for the intended purpose) functional and/or chemical characteristics, as one of ordinary skill in the art will appreciate. Conservative amino acid substitutions are often ones in which the amino acid residue is replaced with an amino acid residue with a similar side chain. Families of amino acid residues having similar side chains have been defined in the art. For examples, lysine, arginine, histidine for basic side chains, aspartic acid and glutamic acid for acidic side chains, glycine, asparagines, glutamine, serine, threonine, tyrosine, cysteine, tryptophan for uncharged polar side chains, alanine, valine, leucine, threonine, isoleucine, proline, phenylalanine, methionine for non-polar side chains, and tyrosine, phenylalanine, tryptophan, histidine for aromatic side chains. The substitution is of amino acids with generally similar physiochemical properties such that the substitutions do not substantially alter peptide, polypeptide or protein characteristics, or activity.

Percent identity between two amino acid sequences is a function of the number of amino acid positions shared by the sequences (i.e. a number of the positions with the same amino acid divided by total number of positions multiplied by 100), taking into account the number of gaps, and length of each gap, which need to be introduced for optimal alignment of the two sequences. Antibodies of the present invention also include those in which modification have been made to the framework residues within $V_H$ and/or $V_L$ to improve one or more properties of the antibody. Typically, such framework modifications are made to decrease the immunogenecity or improve the stability of the antibody.

In addition to modifications made within the framework or CDR regions, antibodies of the invention may be engineered to include modifications within the $F_c$ region, typically to alter one or more functional properties of the antibody, such as serum half life, complement fixation, $F_c$ receptor binding, and/or antigen dependent cellular cytotoxicity. Antibody fragments or derived agents are a part of antibodies or antibodies in a different format comprising a portion that binds to an antigen, and optionally, a scaffold or framework portion that allows the antigen-binding portion of the antigen-binding protein to the antigen. For example, changes in framework or CDR, such as amino acid substitutions, deletions, or additions, can be made yet to maintain its antigen-binding ability. Alternatively, antigen-binding portion of the invention can be derivatized or linked to another molecule (e.g., another peptide, protein, polymers, or chemicals).

Antigen-binding portion of antibodies can be modified to a single chain antibody, a diabody, a triabody, a tetrabody, a $F_{ab}$ fragment (monovalent fragment with $V_L$, $C_L$, $V_H$, and $C_{H1}$), a $F_{(ab')2}$ fragment (two $F_{ab}$ fragments linked by a disulfide bridge), $F_d$ ($V_H$ and $C_{H1}$ domains), scF$_v$ ($V_L$ and $V_H$ is joined by a linker), a domain antibody, bispecific antibodies, a minibody, a scab (an antibody fragment containing $V_H$ and $V_L$ as well as either $C_L$ or $C_{H1}$), an IgD antibody, an IgE antibody, an IgM antibody, an IgG1 antibody, an IgG2 antibody, an Ig3 antibody, an IgG4 antibody, or any derivatives of antibody constant domain, and artificial antibodies based upon protein scaffolds, including, but not limited to, fibronectin type, avimers, or cytochrome B.

Detailed Description of the Invention

The present invention provides isolated recombinant and/or synthetic antibodies against glucagon receptor, as well as compositions and nucleic acid molecules comprising at least one polynucleotide encoding at least one anti-glucagon receptor antibody. This invention provides compositions and methods based on, but not limited to, interfering with glucagon receptor signaling by binding to the extracellular portion of glucagon receptor. Antagonists of the invention, as described herein, provide important therapeutic and diagnostic agents for use in targeting pathological conditions associated with diabetes mellitus and related disease. Accordingly, the invention provides methods, compositions, kits, and articles of manufacture related to modulating glucagon receptor pathway.

In one aspect, the invention provides anti-glucagon receptor therapeutic agents suitable for therapeutic use and capable of effecting varying degrees of disruption of the glucagon receptor signaling pathway. For example, the invention provides human antibodies against glucagon receptor, and derivatives and fragments thereof, comprising a sequence of polynucleotides that encode all or a portion of a polypeptide that binds to the glucagon receptor, such as nucleic acid encoding all or part of an anti-glucagon receptor antibody, antibody fragment, or antibody derivative.

In one embodiment, an antibody of the invention is a human antibody that inhibits binding of human glucagon and glucagon receptor. For example, an antibody of the invention inhibits glucagon binding with an $IC_{50}$ value of less than 1 µM, preferably less than 100 nM, more preferably 10 nM, and most preferably 1 nM. In another embodiment, an antibody of the invention is an antibody that inhibits cAMP signaling dependent on glucagon.

In another embodiment, the present invention provides isolated glucagon receptor specific antibody molecules which comprise heavy and/or light chain variable regions comprising amino acid sequences that are homologous to the corresponding amino acid sequences of the disclosed antibodies, wherein the antibody molecules inhibit glucagon mediated signaling through glucagon receptor. For example, the heavy chain variable domain may comprise a sequence of amino acids that is at least 80, 85, 90, 95, 97 or 99% identical to the sequence of a heavy chain variable domain selected from the group consisting of SEQ ID Nos. 2, 4, 6, 8, 10, 12, 14 and 16. Further, the light chain variable domain may comprise a sequence of amino acids that is at least 80, 85, 90, 95, 97 or 99% identical to the sequence of a light chain variable domain selected from the group consisting of SEQ ID Nos. 18, 20, 22, 24, 26, 28 and 30. Specific embodiments are antagonists which comprise heavy and/or light chain variable regions which are at least 85%, preferably 90%, more preferably 95%, and most preferably 99% homologous to disclosed heavy and/or light chain variable regions, respectively.

In yet another embodiment, the isolated antigen-binding protein comprises a combination of a light chain variable domain and a heavy chain variable domain selected from the group of combinations consisting of a heavy and light chain in SEQ ID Nos. In a specific embodiment, the present invention provides isolated antibody molecules comprising a variant of the heavy and/or light chain variable domain sequences depicted in SEQ ID Nos. 2, 4, 6, 8, 10, 12, 14, 16, 18, 20, 22, 24, 26, 28 and 30, and conservative modifications thereof. In another embodiment, this invention includes antibodies that can be formed by any combination of the variable domains from each light chain and heavy chain sequence as shown in SEQ ID Nos. 2, 4, 6, 8, 10, 12, 14, 16, 18, 20, 22, 24, 26, 28 and 30, and equivalents thereof characterized by having one or more conservative amino acid substitutions in any one or more of the CDR sequences, specific embodiments of which inhibit glucagon dependent activation of glucagon receptor signaling pathway.

The invention also provides chimeric molecules comprising glucagon receptor antagonist linked or fused to another, heterologous polypeptide or polymer. For instance, techniques are known for deriving an antibody of a different subclass or isotype from an antibody of interest, i.e., subclass switching. These include a humanized antibody, chimeric antibody, a monoclonal antibody, a polyclonal antibody, a recombinant antibody, an antigen-binding antibody fragment such as $F_{(ab')2}$, $F_{ab}$, $F_v$, $F_{ab'}$, $F_c$, and $F_d$ fragments, and can be incorporated into single domain antibodies, such as single chain antibodies, maxibodies, minibodies, intrabodies, diabodies, triabodies, tetrabodioes, vNAR and bisscF$_v$ (Hollinger, P. and Hudson, P. J., 2005, *Nat Biotech*, 23: 112636).

In additional embodiments, antibodies, fragments, and derivatives of the invention can be fused to other polypeptides or chemicals. The fusion partner can be a peptide, a protein, or a derivative of an antibody that has specific binding activity to other proteins to create bispecific or multispecific molecules or to improve the physiochemical properties of the molecules. In addition, antibodies can be modified to be glycosylated, pegylated, crosslinked, or conjugated to other proteins or chemicals. Amino acids of antibodies can be substituted by non-natural amino acids.

Glucagon receptor antibodies may carry or be conjugated to a toxin, radioactive isotope, radionuclide, a liposome, a targeting moiety, a biosensor, a cationic tail, or an enzyme. Such antagonist compositions form an additional aspect of the present invention.

In some instances, it may be advantageous to have a glucagon receptor antagonist antibody that does not interfere with binding of the ligand (such as glucagon) to the receptor. Accordingly, in one embodiment, the invention provides an antibody that does not bind a glucagon binding site on glucagon receptor. In another embodiment, an antibody of the invention does not substantially inhibit glucagon binding to glucagon receptor. In another embodiment, an antibody of the invention does not substantially compete with glucagon for binding to glucagon receptor.

In another aspect, the invention provides use of a glucagon receptor antagonist antibody of the invention in the preparation of a medicament for the therapeutic and/or prophylactic treatment of a disease, such as diabetes.

In yet another aspect, the invention provides use of an expression vector of the invention in the preparation of a medicament for the therapeutic and/or prophylactic treatment of a disease, such as diabetes.

In a further aspect, the invention provides use of a host cell of the invention in the preparation of a medicament for the therapeutic and/or prophylactic treatment of a disease, such as diabetes.

In still a further aspect, the invention provides use of an article of manufacture of the invention in the preparation of a medicament for the therapeutic and/or prophylactic treatment of a disease, such as diabetes.

The invention also provides pharmaceutical compositions comprising an antibody, or antigen-binding portion thereof, of the invention and a pharmaceutically acceptable carrier. In one embodiment, the pharmaceutical composition further comprises at least one additional therapeutic agent for treating a disorder in which glucagon receptor activation is detrimental.

The antibodies and antigen-binding portions of the invention can be incorporated into pharmaceutical compositions suitable for administration to a subject. Typically, the pharmaceutical composition comprises an antibody or antigen-binding portion of the invention and a pharmaceutically acceptable carrier. As used herein, 'pharmaceutically acceptable carrier' includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antigen-binding portion.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies.

The antibodies and antigen-binding portions of the present invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results.

Supplementary active compounds can also be incorporated into the compositions. In certain embodiments, an antibody or antigen-binding portion of the invention is coformulated with and/or co-administered with one or more additional therapeutic agents that are useful for treating disorders in which glucagon receptor activation is detrimental. For example, an anti-glucagon receptor antibody or antigen-binding portion of the invention may be co-formulated and/or co-administered with one or more additional antibodies that bind other targets. Furthermore, one or more antibodies of the invention may be used in combination with two or more of therapeutic agents. Such combination therapies may advantageously utilize lower dosages of the administered therapeutic agents, thus avoiding possible toxicities or complications associated with the various monotherapies.

The pharmaceutical compositions of the invention may include a 'therapeutically effective amount' or a 'prophylactically effective amount' of an antibody or antigen-binding portion of the invention. A 'therapeutically effective amount' refers to an amount effective, at dosages and for periods of time necessary, to achieve the desired therapeutic result. A therapeutically effective amount of the antibody or antigen binding portion may vary according to factors such as the disease state, age, sex, and weight of the individual, and the ability of the antibody or antigen-binding portion to elicit a desired response in the individual. A therapeutically effective amount is also one in which any toxic or detrimental effects of the antibody or antigen-binding portion are outweighed by the therapeutically beneficial effects. A 'prophylactically effective amount' refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

An exemplary, non-limiting range for a therapeutically or prophylactically effective amount of an antibody or antigen-binding portion of the invention is 0.01-100 mg/kg, more preferably 0.1-30 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Hereinafter, the present invention will be specifically explained with reference to the following examples, which are provided only for the better understanding of the invention, but should not be construed to limit the scope of the invention in any manner.

EXAMPLE 1

Screening of Antibodies that Bind to Glucagon Receptor

HEK293 and CHO cells expressing full length human glucagon receptor with GFP fusion at C-terminus were generated. The stable pool was sorted by FACS and highly fluorescent cells were sorted to enrich cells expressing glucagon receptor in high level.

To generate the protein that encodes the $1^{st}$ extracellular domain of human glucagon receptor, a mammalian expression vector consisting $1^{st}$ extracellular domain of human glucagon receptor was fused to the $F_c$ portion of human IgG1 at the C-terminus (NTD-$F_c$). The construct was transfected into HEK293 cells transiently and the conditioned media was harvested. NTD-$F_c$ fusion protein was purified using protein A agarose beads (Pierce) by affinity purification.

NTD-$F_c$ and cells expressing glucagon receptor were used to pan against phage library displaying $scF_v$ of human antibodies. $scF_v$ was prepared from human cDNA generated from healthy human beings and displayed on M13 phage using pIII fusion. For panning, purified NTD-$F_c$ was immobilized on protein G magnetic beads (Invitrogen) and bound phages were eluted with triethylamine for the first round. HEK293 cells and CHO cells expressing glucagon receptor with GFP fusion were used in subsequent rounds of panning. After 3 rounds of panning, individual phage clones were examined for its ability to bind NTD-$F_c$ in ELISA. The positive phages were then tested for binding in cell based ELISA in CHO or HEK293 cells expressing glucagon receptor fused to GFP.

EXAMPLE 2

Antibody Conversion and Activity Test

Selected phage clones were sequenced and unique clones were converted into human IgG2 to produce fully human antibodies by transient expression. Conditioned media was harvested and antibodies were purified using protein A agarose beads (Pierce). Various amounts of antibodies were then prepared for cell based ELISA to test its binding ability to human glucagon receptor.

The purified antibodies were then tested for neutralizing activity in cAMP assay using cAMP HTRF kit (CisBio). Various amounts of antibodies were added to the cells expressing glucagon receptor and incubated for 15 minutes before glucagon was added to the cells. Stimulation of glucagon receptor was measured by the amount of cAMP production. Potency of antibody was determined by percentage of inhibition of cAMP production at 100 pM of glucagon stimulation.

EXAMPLE 3

In Vivo Efficacy Test of Antibodies in High Fat Induced Obesity Model

To test the in vivo efficacy of antibodies, Ab7 was transiently expressed and purified. After protein A purification, antibody was quantified and confirmed its activity in cAMP assay.

For high fat diet-induced obesity model, C57BL/6 male mice were acclimated and fed a highfat diet (60% fat by calories; Research Diet) for 6 weeks. On the day of administration, mice were bled for baseline blood glucose measurement, followed immediately with body weight measurement. Mice were sorted into 3 groups (n=9~10 per group) having a similar distribution based on body weight and blood glucose. Mice were then given a single intraperitoneal (IP) injection of vehicle or antibody at 7 mg/kg and 1 mg/kg. Subsequent blood glucose measurements were taken at 1, 2, 3, and 10 days after the single injection.

EXAMPLE 4

Molecular Mechanism of the Antibody Effect Examined by Radioisotope Dilution Method To gain further insight into the mechanism of glucose lowering effect of the antibody, hepatic and peripheral insulin sensitivity was assessed by radioisotope-labeled glucose infusion (Choi C. S. et al, *Proc Natl Acad Sci U-S-A,* 2007, 104:16480-85). C57BL/6 male mice were acclimated and fed a high-fat diet (60% fat by calories; Research Diet)for 6 weeks. Seven days before the study, indwelling catheters were placed into the jugular vein. Mice are then given a single intraperitoneal (IP) injection of vehicle or antibody at 7 mg/kg 48h prior to the experiments.

After an overnight fast, [3-$^3$H]-glucose (Perkin Elmer) was infused for 2 hours to assess the basal glucose appearance rate (basal hepatic glucose production). Blood samples (20 μl) were collected at the end of basal period for the measurement of fasting plasma glucose concentration and [3-$^3$H]-glucose activity. Rates of basal whole body glucose appearance were determined as the ratio of the [3-$^3$H]-glucose infusion rate (disintegrations per minute [dpm]) to the specific activity of plasma glucose (dpm per mg) at the end of the basal period.

```
Sequence Listing Free Text
SEQ ID No. 1 represents the nucleotide sequence of heavy chain variable region
HC1;

SEQ ID No. 2 represents the amino acid sequence of heavy chain variable region
HC1;

SEQ ID No. 3 represents the nucleotide sequence of heavy chain variable region
HC2;

SEQ ID No. 4 represents the amino acid sequence of heavy chain variable region
HC2;

SEQ ID No. 5 represents the nucleotide sequence of heavy chain variable region
HC3;

SEQ ID No. 6 represents the amino acid sequence of heavy chain variable region
HC3;

SEQ ID No. 7 represents the nucleotide sequence of heavy chain variable region
HC4;

SEQ ID No. 8 represents the amino acid sequence of heavy chain variable region
HC4;

SEQ ID No. 9 represents the nucleotide sequence of heavy chain variable region
HC5;

SEQ ID No. 10 represents the amino acid sequence of heavy chain variable region
HC5;

SEQ ID No. 11 represents the nucleotide sequence of heavy chain variable region
HC6;

SEQ ID No. 12 represents the amino acid sequence of heavy chain variable region
HC6;

SEQ ID No. 13 represents the nucleotide sequence of heavy chain variable region
HC7;

SEQ ID No. 14 represents the amino acid sequence of heavy chain variable region
HC7;

SEQ ID No. 15 represents the nucleotide sequence of heavy chain variable region
HC8;

SEQ ID No. 16 represents the amino acid sequence of heavy chain variable region
HC8;

SEQ ID No. 17 represents the nucleotide sequence of light chain variable region
LC1;

SEQ ID No. 18 represents the amino acid sequence of light chain variable region
LC1;

SEQ ID No. 19 represents the nucleotide sequence of light chain variable region
LC2;

SEQ ID No. 20 represents the amino acid sequence of light chain variable region
LC2;

SEQ ID No. 21 represents the nucleotide sequence of light chain variable region
LC3;

SEQ ID No. 22 represents the amino acid sequence of light chain variable region
LC3;

SEQ ID No. 23 represents the nucleotide sequence of light chain variable region
LC4;
```

-continued

SEQ ID No. 24 represents the amino acid sequence of light chain variable region LC4;

SEQ ID No. 25 represents the nucleotide sequence of light chain variable region LC5;

SEQ ID No. 26 represents the amino acid sequence of light chain variable region LC5;

SEQ ID No. 27 represents the nucleotide sequence of light chain variable region LC6;

SEQ ID No. 28 represents the amino acid sequence of light chain variable region LC6;

SEQ ID No. 29 represents the nucleotide sequence of light chain variable region LC7; , and SEQ ID No. 30 represents the amino acid sequence of light chain variable region LC7.

---

The invention claimed is:

1. An isolated antibody or an antigen-binding portion thereof for specifically binding to a human glucagon receptor, comprising:
a heavy chain, or a light chain, or both the heavy chain and the light chain, wherein said heavy chain or antigen-binding portion thereof comprises a heavy chain variable region having the amino acid sequence as set forth in SEQ ID No. 12; and said light chain or antigen-binding portion thereof comprises a light chain variable region having the amino acid sequence as set forth in SEQ ID No. 28.

2. The isolated antibody or the antigen-binding portion thereof according to claim 1, which is a monoclonal antibody.

3. The isolated antibody or the antigen-binding portion thereof according to claim 1, wherein the antibody is selected from the group consisting of a human antibody, a humanized antibody, an antigen-binding antibody fragment, a single chain antibody, a diabody, a triabody, a tetrabody, a $F_{ab}$ fragment, a $F_{(ab')2}$ fragment, $F_d$, $scF_v$, a domain antibody, a bispecific antibody, a minibody, a scab, an IgD antibody, an IgE antibody, an IgM antibody, an IgG1 antibody, an IgG2 antibody, an Ig3 antibody, and an IgG4 antibody.

4. A pharmaceutical composition comprising the isolated antibody or the antigen-binding portion thereof according to claim 1, and one or more pharmaceutically acceptable carrier.

* * * * *